United States Patent [19]

Koga et al.

[11] 4,353,784
[45] Oct. 12, 1982

[54] METHOD OF RECOVERY OF ACETIC ACID

[75] Inventors: Kunio Koga, Ohimachi; Ryoichi Kishimoto, Sakai, both of Japan

[73] Assignee: Daicel Chemical Industries, Ltd., Sakai, Japan

[21] Appl. No.: 304,145

[22] Filed: Sep. 21, 1981

[51] Int. Cl.$^3$ .................... B01D 11/04; C07C 51/44; C07C 51/48
[52] U.S. Cl. ..................... 203/16; 203/43; 203/78; 562/608
[58] Field of Search .................. 203/15, 16, 43–46, 203/73, 78, 80, 51, 57, 59, 60, 62, 91, 63, 38; 562/513, 608

[56] References Cited

U.S. PATENT DOCUMENTS

| | | | |
|---|---|---|---|
| 2,568,095 | 9/1951 | Smith et al. | 562/608 |
| 2,571,919 | 10/1951 | Morrell | 562/608 |
| 2,588,268 | 3/1952 | Mercer et al. | 203/16 |
| 2,868,832 | 1/1959 | Taylor et al. | 562/608 |
| 3,394,058 | 7/1968 | Hohenschutz | 203/16 |
| 3,433,831 | 3/1969 | Yomiyama et al. | 562/608 |
| 3,692,829 | 9/1972 | Sennewald nt al. | 562/608 |
| 3,980,702 | 9/1976 | Grinstead | 562/513 |
| 4,143,066 | 3/1979 | Kalcevic | 562/513 |

FOREIGN PATENT DOCUMENTS 55-154935  12/1980  Japan .................. 562/608

OTHER PUBLICATIONS

Wardell et al., Solvent Equilibria for Extraction of Carboxylic Acid from Water: Journal of Chem. & Eng. Data, vol. 23, No. 2, 1978, pp. 144–148.

*Primary Examiner*—Wilbur L. Bascomb, Jr.
*Attorney, Agent, or Firm*—Blanchard, Flynn, Thiel, Boutell & Tanis

[57] ABSTRACT

Disclosed is a method of recovering acetic acid by extracting from an acetic acid-containing aqueous solution with an organic extracting agent and subjecting the extract to distillation, said method comprising the first step of performing extraction by using a tertiary amine having a boiling point higher than that of acetic acid and being capable of forming a non-aqueus phase as the organic extracting agent in combination with an oxygen-containing, high-boiling-point organic solvent selected from the group consisting of di-isobutylcarbinol, isophorene, methyl benzoate, tributyl phosphate, 3,3,5-trimethylcyclohexanone and 2-ethoxyethyl acetate, the second step of performing dehydration by subjecting the extract to distillation, and the third step of subjecting the dehydrated mixture to distillation in a reduced pressure distillation column at a column bottom temperature of 120° to 170° C. to distill acetic acid and separate it from the organic extracting agent.

According to this method, water-free acetic acid can be recovered from an acetic acid-containing aqueous solution at a high separation efficiency with reduced energy consumption, and this recovery method is suitably applied to recovery of acetic acid from acetic acid-containing aqueous solutions discharged from various chemical industrial processes.

13 Claims, 2 Drawing Figures

METHOD OF RECOVERY OF ACETIC ACID

BACKGROUND OF THE INVENTION (1) Field of the Invention

The present invention relates to a method of recovering acetic acid from an acetic acid-containing aqueous solution. More particularly, the present invention relates to a method of recovery of acetic acid which comprises in combination the extraction step using an extracting agent including a tertiary amine and the dehydration and recover step utilizing distillation.

(2) Description of the Prior Art

Acetic acid, acetic anhydride and peracetic acid are used in the organic chemical industries, for example, for manufacture of cellulose acetate, alkyl acetates, ketenes, glycerin and epoxyalkanoic acids, and acetic acid-containing solutions are withdrawn from these processes. For example, acetic acid is formed as a by-product at a concentration of 20 to 40% from the process for production of cellulose acetate, and acetic acid is formed as a by-product at a concentration of 10 to 15% from the process for production of glycerin by the use of peracetic acid. Aqueous solutions containing acetic acid at such medium concentrations of about 7 to about 40% are produced in large quantities as by-products, and effective recovery of acetic acid from such aqueous solutions are indispensable and important for increasing economical efficiencies of the main processes. Furthermore, acetic acid is used in other fields, for example, in the metal treatments industries and in the fermentation industries, and also in these fields, there are formed aqueous solutions containing acetic acid. In order to enhance the utilization ratios of valuable substances and prevent occurrence of environmental pollution, it is very important to recover acetic acid at high efficiencies from these acetic acid-containing solutions.

An extraction method using an organic solvent is known as means for recovering a carboxylic acid from an aqueous solution, and this method can be applied to the recovery of acetic acid. Among carboxylic acids, acetic acid has a high affinity with water, and although various compounds have been used as extracting agents for the recovery of acetic acid, none of them have proved to provide satisfactory results. More specifically, the distribution coefficient, which has significant influences on the efficiency of the recovery by extraction, is ordinarily very small in case of acetic acid, and therefore, in order to increase the extraction ratio, it is necessary to use a large amount of a solvent, which results in increase of the energy consumption at the separation step.

Distribution coefficients to dilute aqueous solutions of acetic acid, shown by Treybal and Won, which are cited by J. M. Wardell and C. J. King in J. Chem. Eng. Data, 23 (2), 144 [1978], are as follows:

| Ethers ($C_4$-$C_8$) | 0.63–0.14 |
|---|---|
| Acetates ($C_4$-$C_{10}$) | 0.89–0.17 |
| Ketones ($C_4$-$C_{10}$) | 1.20–0.61 |
| Alcohols ($C_4$-$C_8$) | 1.68–0.64 |

Among these extracting agents, ethyl acetate has a relatively large distribution coefficient to acetic acid (0.9 to 1.0) and is easily available, and therefore, ethyl acetate is customarily used as the extracting agent for recovery of acetic acid. However, since the boiling point of ethyl acetate is lower than that of acetic acid, all of the solvent used in a large amount should completely be evaporated. Furthermore, a large amount of water is dissolved in the extract and loss by dissolution in water is considerable. Accordingly, ethyl acetate as the extracting agent is unsatisfactory also with respect to the mutual solubility with water.

There has been proposed an extraction method using an extracting agent having a boiling point higher than that of acetic acid. If there is a solvent having a distribution coefficient comparable to that of a low-boiling-point solvent, which is applicable to this extraction method, since all of the solvent used need not be evaporated, this method is economically advantageous because the energy consumption is reduced. However, it the boiling point of the solvent is too high, the column bottom heating temperature cannot sufficiently be provided by steam ordinarily available in a chemical plant. If reduced pressure distillation is carried out for overcoming this disadvantage, condensation of the distillate cannot sufficiently be accomplished by ordinary cooling water.

These difficulties involved in heating and cooling can be eliminated by using a solvent having a boiling point higher than that of acetic acid but lower than 150° C., such as isoamyl acetate, as disclosed in U.S. Pat. No. 1,839,894. However, separation of the solvent from acetic acid becomes difficult, and the amount of the solvents dissolved in water is increased.

As will be apparent from the foregoing description, satisfactory recovery of acetic acid cannot be attained by any methods based on the principle of the physical distribution of acetic acid between the organic phase and the aqueous phase.

There also is known a method in which an acid in an aqueous solution is extracted with an amine, which is a basic organic liquid, by the use of chemical reaction. For example, in the field of a chemical treatment of a nuclear fuel or a wet refining treatment of a metal, a high-molecular-weight amine, together with a diluent such as kerosene or an aromatic hydrocarbon, is used for extraction of an inorganic acid.

Such waste acid treatment using an amine has been known in the field of metal industries. However, separation of an acid from an extract is ordinarily accomplished by stripping with water, and it is not true that water-free phosphoric acid or sulfuric acid is recovered by the above method. In this point, recovery of inorganic acids is different from recovery of acetic acid in organic chemical industries where acetic acid should be recovered in the for of a water-free pure product.

Inoue et al. have published the results of researches made on the equilibrium of extraction of acetic acid with a high-molecular-weight amine and the extraction speed [Kagaku Kōgaku, 33, page 1221 and Kagaku Kogaku Ronbun Shu 5 (2), page 212]. The amine used by Inoue et al. is a high-molecular-weight secondary amine having 24 to 27 carbon atoms as a whole, namely N-lauryl-(trialkylmethyl) amine (LA-2), and this amine is used in combination with a solvent such as chloroform, carbon tetrachloride, MIBK, n-hexane or cyclohexane.

SUMMARY OF THE INVENTION

We made researches on the method of recovering water-free acetic acid by extracting acetic acid from an acetic acid-containing aqueous solution with an organic liquid containing a basic compound and recovering water-free acetic acid from the extract by distillation. We found that the method using the secondary amine taught by Inoue et al. is suitable for extraction per se but is not suitable for recovery by distillation because the bondage between the amine and acetic acid is too strong. It also was found that if a tertiary amine having a weaker bonding force to acetic acid is used in combination with a specific solvent, water-free acetic acid can be recovered with reduced energy consumption.

More specifically, in accordance with the present invention, there is provided a method of recovering acetic acid by extracting an acetic acid-containing aqueous solution with an organic extracting agent and subjecting the extract to distillation, said method comprising the first step of performing extraction by using a tertiary amine having a boiling point higher than that of acetic acid and being capable of forming a non-aqueous phase as the organic extracting agent in combination with an oxygen-containing, high-boiling-point organic solvent selected from the group consisting of diisobutylcarbanol, isophorone, methyl benzoate, tributyl phosphate, 3,3,5-trimethylcyclohexanone and 2-ethoxyethyl acetate, the second step of performing dehydration by subjecting the extract to distillation, and the third step of subjecting the dehydrated mixture to distillation in a reduced pressure distillation column at a column bottom temperature of 120° to 170° C. to distill acetic acid and separate it from the organic extracting agent.

According to one preferred embodiment of the abovementioned recovery method of the present invention, an extractor which is designed so that the frequency of dispersion and integration of liquid drops is promoted, such as a mixer-settler type extraction device, is used, and acetic acid is extracted from an aqueous solution containing acetic acid by using a tertiary amine such as tri-n-octylamine (hereinafter referred to as "TOA") in combination with an oxygen-containing organic solvent such as 3,3,5-trimethylcyclohexanone (hereinafter referred to as "TMCH") (each having a boiling point higher than that of acetic acid). The obtained extract is fed to a dehydration distillation column where a small amount of water included in the extract is removed therefrom, and the dehydrated extract is fed to an acetic acid recovery column. Water-free acetic acid is recovered from the top of the column and the regenerated extracting agent is recovered from the column bottom. If the column bottom temperature is maintained at about 120° C. to about 150° C. at this step, separation of acetic acid from the extracting agent can be accomplished very smoothly. Furthermore, heating can be performed by using, as a heat source, steam customarily used in a chemical plant. A part of the regenerated extracting agent recovered from the column bottom is introduced to the top of the dehydration distillation column and is used as a reflux liquid in the dehydration distillation column. If this arrangement is adopted, acetic acid which is likely to rise in the column together with water and the oxygen-containing compound is extracted with the tertiary amine-containing reflux liquid and is brought down, whereby distillate of acetic acid from the dehydration distillation column can be prevented. The regenerated extracting agent (for example, TOA+TMCH) withdrawn from the bottom of the acetic acid recovery column is recycled to the extracting device of the first step and used again.

Several methods using an extracting agent including an amine are found in the prior art techniques of extracting acetic acid contained at a low concentration in waste water. For example, Wardell has proposed a method in which acetic acid is recovered from the starting solution containing 0.5% of acetic acid by using TOA together with chloroform as a diluent [see J. Chem. Eng. Data, 23 (2), 144 (1978)]. Chloroform per se is a low-boiling point solvent, but use of other diluents such as hexanol is taught by Wardell. Hexanol is an oxygen-containing organic solvent having a boiling higher than that of acetic acid, and it is very close to the diluent used at the first step of the method of the present invention. However, hexanol cannot be used in the method of the present invention because hexanol is esterified with acetic acid and no good results can be obtained. In this prior art reference, equilibrium at the extraction step is discussed, but the adaptability of the extracting agent to recovery of acetic acid from the extract or to recycle and repeated use of the extraction agent is not touched at all.

In the report submitted for the symposium "Absorption and Extraction" held at the annual meeting (November 1977) of the American Institute of Chemical Engineers, Ricker et al. discussed extraction with an amine in the treatment of waste water from the acetic acid industry and pointed out the problem of esterification in the combined use of amines and alcohols and they taught that use of 2-ethyl hexanol and low temperature regeneration (vacuum distillation or steam stripping) are effective for prevention of esterification. Incidentally, the acetic acid concentration in the waste water discussed in this report is about 1%.

The thesis for a degree submitted by Ricker to University of California, Berkeley in 1978, it is taught that a linear ketone such as 2-heptanone, methylisoamyl ketone or di-isobutyl ketone is used as a solvent to be combined with a tertiary amine, and also the acetic acid recovery flow sheet including not only the extraction step but also a solvent-regenerating column is disclosed. Separation of acetic acid from the mixed solvent is conducted in an atmospheric pressure distillation column where the column bottom temperature is 175° C.

Furthermore, Japanese Patent Application Laid-Open Specification No. 154935/80 discloses a method in which an organic acid is recovered by extraction with a mixed solvent including an amine. In this method, however, a petroleum type hydrocarbon is used as the diluting solvent, and in Examples, a mixture of a petroleum type hydrocarbon and a secondary amine is used. In this prior art reference, it is taught that distillation can be adopted for separation of acetic acid from the extracted mixture, but only the solvent vapor pressure is mentioned as the basis thereof and no specific embodiment of the separation by distillation is given. The stripping method using an aqueous solution containing Na is specifically disclosed and recommended.

The present invention will now be desdribed in detail while comparing it with the above-mentioned prior art techniques.

BRIEF DESCRIPTION OF THE DRAWINGS

FIG. 1 is a diagram illustrating the apparent distribution coefficient of acetic acid into a TOA/TMCH mixed solvent as a function of the acetic acid concentration in the equilibritated aqueous phase.

FIG. 2 is a diagram illustrating the apparent distribution coefficient (S/F=1.0, 30° C.) into a TOA/TMCH mixed solvent measured at various charge acetic acid concentrations as a function of the composition of the mixed solvent.

DETAILED DESCRIPTION OF THE PREFERRED EMBODIMENTS

Tertiary amines having a boiling point higher than that of acetic acid and being capable of forming a nonaqueous phase are used in the present invention. In view of the low solubility into the aqueous phase and the separability from acetic acid, it is preferred that a tertiary amine having about 12 to about 40 carbon atoms be used. Furthermore, in order to obtain a large apparent distribution coefficient, it is preferred that a tertiary amine having no large branch in the vicinity of the nitrogen atom be used. The presence of a substituent larger than an ethyl group not only at the position adjacent to the nitrogen atom but also on the carbon atom separate from the nitrogen atom through one $-CH_2$ group has bad influences, and a substituent having a cyclic structure close to the nitrogen atom, such as a benzyl group, is not preferred. If a part of the tertiary amine is expressed by the formula $>N-CH_2-CR^1R^2-$, an amine in which $R^1$ is a hydrogen atom and $R^2$ is a hydrogen atom or methyl group should be selected. As preferred tertiary amines, there can be mentioned trialkyl amines containing an alkyl group having at least 6 carbon atoms, such as trihexylamine, tri-isoctylamine (tris-2,4,4-trimethylpentylamine), trilaurylamine, dimethyllaurylamine, dimethylhexadecylamine, methyl-di (tridecyl)amine and dimethyldecylamine, tertiary amines containing an alkenyl group, such as dimethyloleylamine and butyl-bis(5,5,7,7-tetramethyl-octo-2-en-1-yl)amine (XE-204), and tertiary amine mixtures such as dimethyl coco-amine, dimethyl $C_{8-12}$-alkyl amine and dimethyl hydrogenated beef-tallow amine. Among these tertiary amines, commercially available products can be used directly, and tertiary amines prepared by converting primary or secondary amines as intermediates according to the known alkylation method can also be used. In the present invention, various tertiary amines can be used, but in practising the method of the present invention, TOA is mainly used because it is easily available and if it is used in combination with an oxygen-containing organic solvent as an extracting agent, an excellent apparent distribution coefficient is obtained.

In the field of refining of metals, a non-polar solvent such as kerosene or an aromatic hydrocarbon is used in combination with an amine, and in the report of Inoue et al., it is taught that a low-boiling-point solvent composed mainly of a solvent having a low polarity, such as a hydrocarbon or a chlorinated hydrocarbon, is used in combination with a secondary amine. In contrast, according to the present invention, by using an oxygen-containing organic solvent having a boiling point higher than that of acetic acid, such as a ketone, an alcohol, a carboxylic acid ester or a phosphoric acid ester, in combination with a tertiary amine such as mentioned above, acetic acid can be extracted from an aqueous solution with a considerably large apparent distribution coefficient.

By the term "apparent distribution coefficient" used in the instant specification is meant the ratio of the acetic acid concentrations in the organic phase and aqueous phase between which the equilibrium relation is established. Acetic acid is present in the form of a monomer, a dimer, an oligomer and so on coupled with the amine according to the kind of the solvent and the acetic acid concentration, and therefore, the apparent distribution coefficiency changes according to the concentration contrary to the theoretical rule of distribution.

The values of the apparent distribution coefficient m determined as a function of the acetic acid concentration x in the aqueous phase in case of the combined use of TOA and TMCH are shown in FIG. 1. When TMCH which is an oxygen-containing organic solvent is used alone, the influence of the acetic acid concentration is not significant and the apparent distribution coefficient is about 0.5. Similar tendencies are observed in case of other ketones, acetates, ethers and alcohols. On the other hand, in case of TOA, the influence of the acetic acid concentration in the aqueous phase is very significant. It has been found that when TOA is used in combination with TMCH, the apparent distribution coefficient is several times the apparent distribution coefficient attained when TMCH alone is used and at certain acid concentrations, the apparent distribution coefficient is often larger than the apparent distribution coefficient attained when TOA alone is used. At an acetic acid concentration of 0 to 5% in the aqueous phase, an especially large distribution coefficient can be obtained by the combined used of the tertiary amine and oxygen-containing solvent. This acetic acid concentration range corresponds to the actual concentration in the aqueous phase in the field of organic chemical industries where acetic acid is recovered from an aqueous solution containing about 10 to about 40% of acetic acid. Therefore, the above-mentioned fact is very advantageous from the industrial viewpoint.

When an aqueous solution containing 28% of acetic acid was extracted by means of a five-stage mixer-settler, acetic acid contents in lower layers (aqueous phase) of respective settler stages were determined. At that time the solvent mixture of TOA and TMCH (1:1) to the feed stock (S/F) was 1.0 and the extraction temperature was 30° C. Results are given below.

| the first stage | 12.27% |
|---|---|
| second | 2.46 |
| third | 0.69 |
| fourth | 0.20 |
| fifth | 0.05 |

Another extraction test was conducted in the same way as above, except for using a seven-stage apparatus and changing temperatures. Acetic acid contents in respective aqueous phases are listed in TAble 1. The feeding temperature was 30° C.

TABLE 1

| temp. | stage | | | | | | |
|---|---|---|---|---|---|---|---|
| | 1 | 2 | 3 | 4 | 5 | 6 | 7 |
| 50° | 15.2 | 4.8 | 2.1 | 1.1 | 0.60 | 0.29 | 0.13 |
| 40° | 15.0 | 4.4 | 1.6 | 0.7 | 0.35 | 0.17 | 0.08 |
| 30° | 13.0 | 3.5 | 1.2 | 0.6 | 0.27 | 0.13 | 0.06 |

It is seen from the above that the maximum distribution coefficiency as shown in FIG. 1 falls within the actual acetic acid contents in the aqueous phase and therefore are practicable.

The above-mentioned Wardell et al. reference merely discusses the distribution coefficient in case of extraction of acetic acid from a 0.5% acetic acid solution, and the Ricker et al. reference is directed to recovery of acetic acid from waste water having a low acetic acid concentration. It has been clarified for the first time by the present invention that in extraction of acetic acid from an aqueous solution containing acetic acid at a medium concentration of 7 to 40%, a high-boiling point mixed solvent including a tertiary amine gives very desirable results.

As pointed out hereinbefore, a large apparent distribution coefficient can be obtained by using an oxygen-containing organic solvent and a tertiary amine in combination. However, the value of the apparent distribution coefficient and the change of this value according to the acetic acid concentration in the aqueous phase vary greatly depending on the kind of the oxygen-containing organic solvent.

More specifically, when isoamyl acetate, cyclohexyl acetate, di-isobutyl ketone, trioctyl phosphate or the like is used in combination with TOA at a 50/50 volume ratio, a dancette line of the distribution coefficient similar to the 50% line in FIG. 1 is obtained, but the absolute value is relatively small and especially small at a low acetic acid concentration in the aqueous phase (about 1.5 at an acetic acid concentration of 0.4%). In this point, this mixed solvent is inferior to TOA-TMCH.

Some solvent provides at a low acetic acid concentration in the aqueous phase a larger apparent distribution coefficient than that attainable by TOA-TMCH when it is used in combination with TOA at a 50/50 volume ratio. As such solvent, there can be mentioned tributyl phosphate (apparent distribution coefficients of 2.67 and 3.50 at acetic acid concentrations x of 0.26 and 2.04%, respectively), isophorone (apparent distribution coefficients of 3.67 and 5.69 at acetic acid concentrations x of 0.23 and 1.35%, respectively), methyl benzoate (apparent distribution coefficients of 2.31 and 4.06 at acetic acid concentrations x of 0.28 and 1.60%, respectively) and 2-ethoxyethyl acetate (apparent distribution coefficients of 2.9 and 6.0 at acetic acid concentrations x of 0.2 and 1.3%, respectively). Furthermore, di-isobutyl carbinol (hereinafter referred to as "DIBC") shows extremely large distribution coefficients at low acetic acid concentrations (8.20 and 4.27 at acetic acid concentrations x of 0.10 and 1.77%, respectively), and shows a tendency different from the tendency indicated by the dancette line of the distribution coefficient shown in FIG. 1.

Combinations of the foregoing solvents with TOA provide apparent distribution coefficients (2 to 3 at acetic acid concentrations x of 7 to 10%) comparable to the apparent distribution coefficient attained by the combination of TMCA-TOA at relatively high acetic acid concentrations in the aqueous phase.

As is seen from the foregoing description, the distribution coefficient is influenced by both the acetic acid concentration in the aqueous phase and the kind of the mixed solvent. Accordingly, the kind of the solvent selected at an acetic acid concentration of at least 7% is different from the kind of the solvent selected at a low acetic acid concentration of about 1%.

We noted that recovery of acetic acid from an aqueous solution having an acetic acid concentration which is at least 5%, particularly about 7 to about 40%, is industrially important, and we made researches with a view to developing a recovery method suitably applicable to such acetic acid aqueous solutions. As the result, it has been found that this object can be attained by using a specific oxygen-containing organic solvent and a tertiary amine.

As the specific oxygen-containing organic solvent, there can first be mentioned 3,3,5-trimethylcyclohexanone which is alicyclic ketone. As pointed out hereinbefore, the distribution coefficient attained by a mixture of this solvent and TOA is suitable for attaining the object of the present invention. isophorone which also is an alicyclic ketone gives at an acetic acid concentration of 2 to 3% in the aqueous phase a distribution coefficient of about 6 higher than the distribution coefficient attained by TMCH-TOA when it is used in combination with TOA. When DIBK referred to in the thesis of Ricker is combined with TOA, smaller distribution coefficients (1.47, 2.76 and 2.29 at acetic acid concentrations of 0.41, 2.55 and 8.03%, respectively) are obtained.

When a certain high-boiling-point ester is combined with TOA, a larger distribution coefficient is obtained. For example, when 2-ethoxyethyl acetate is combined with TOA, a peak of the distribution coefficient of about 7 can be obtained at an acetic acid concentration of 2 to 3% in the aqueous phase, and methyl benzoate-TOA and tributyl phosphate-TOA give large distribution coefficients. However, even if such high-boiling-point esters as cyclohexyl acetate and trioctyl phosphate are combined with TOA, such large distribution coefficients cannot be obtained (in case of the latter combination, the distribution coefficient is 2.37 at an acetic acid concentration of 2.92%).

Among the solvent systems used in the present invention, DIBC-TOA shows a somewhat different tendency. Namely, this mixture shows an extremely large distribution coefficient at a low acetic acid concentration, as pointed out hereinbefore. A similar tendency is observed in case of a mixture of TOA with chloroform which is a low-boiling-point solvent. However, this tendency is peculiar in the present invention where high-boiling-point solvents are used. DIBC is a secondary alcohol having two large substituents, and therefore, this alcohol is advantageous over a primary alcohol such as hexanol or 2-ethylhexanol in that the change of the composition of the mixed solvent by esterification is remarkably reduced.

When the above-mentioned preferred tertiary amines other than TOA are used, there are observed tendencies similar to those described above. When tris-2-ethylhexylamine which contains a hydrocarbon chain branch located in the vicinity of the nitrogen atom is used as the tertiary amine, the apparent distribution coefficient to acetic acid is much smaller than that obtained by using TOA which is an isomer of tris-2-ethylhexylamine (50/50 mixture of tris-2-ethylhexylamine and TMCH shows apparent distribution coefficients of 0.16, 0.17 and 0.21 at acetic acid concentrations of 0.85, 8.71 and 24.95% in water, respectively). However, a mixture of tri-iso-octylamine and TMCH shows an apparent distribution coefficient only slightly smaller than the apparent distribution coefficient attained by TOA/TMCH (tri-iso-octylamine/TMCH shows apparent distribution coefficients of 1.06, 2.90 and 2.55 at acetic acid concentrations of 0.51, 2.54 and 8.09%, respectively). Accordingly, the apparent distribution coefficient greatly differs among isomers. Incidentally, it was found that when dimethylbenzylamine having a circular branch at the 2-position is used, the apparent distribution coefficient is smaller than 0.1.

The mixing ratio of the tertiary amine to the oxygen-containing organic compounds can optionally be changed according to the intended object. As is seen from FIG. 2, when the charge acetic acid concentration is 10% or lower, a high synergistic effect of improving the apparent distribution coefficient when the mixing ratio is about 50/50 is obtained. Also when the charge acetic acid concentration is as high as 30%, since the acetic acid concentration in the liquid supplied to second and subsequent extracting devices is low, the synergistic effect attained at a mixing ratio of about 50/50 is important. When the amount of the tertiary amine is too large, the method becomes disadvantageous with respect to the cost and distribution coefficient, and if the amount of the tertiary amine is too small, the intended large distribution coefficient cannot be attained. Accordingly, the tertiary amine is ordinarily used in an amount of 10 to 80% by volume.

The temperatures of acetic acid-containing aqueous solutions differ according to the process steps where these aqueous solutions are formed. A dilute acetic acid solution maintained at normal temperatures or lower temperatures may directly be supplied to the extraction step, but when a high-temperature dilute acetic acid solution is treated, it is preferred that the extraction temperature be lowered by cooling. For example, the distribution coefficients are 2.69, 2.40, 2.09 and 1.80 at 20°, 40°, 60° and 80° C., respectively. Thus, it has been confirmed that the distribution coefficient is linearly reduced with elevation of the temperature. Incidentally, each of the values of distribution coefficients mentioned above is one determined at 30° C., and if the measurement temperature is lower, larger values are obtained. From the results of extraction experiments conducted in a mixer-settler type extracting device, it has been confirmed that the acetic acid concentrations in the extraction residues are 0.25% at 50° C., 0.18% at 40° C. and 0.14% at 30° C. and better results can be obtained at a lower extraction temperature.

The S/F ratio, that is, the ratio of the amount charged of the extracting agent to the amount charged of the dilute acetic acid solution, can be changed according to the concentration of the acetic acid and the intended object. In the present invention, by virtue of a characteristic large distribution coefficient, the S/F ratio can be lowered to 0.5 to 2. In the present invention, the amount used of the extracting agent can thus be reduced, and therefore, the apparatus size and running cost can be decreased industrially advantageously.

The extraction step, which is the first step of the method of the present invention can be performed in various apparatuses in which two liquid phases are brought into contact with each other. In order to perform this step at a high efficiency, it is preferred that an apparatus of the type where the interface between the two liquid phases is frequently refreshed be used. In the chemical industries, as the continuous extracting device, there are ordinarily used packed columns, perforated plate columns and ring and plate columns. It has been found that good results cannot always be obtained by these apparatuses in the method of the present invention. To our great surprise, however, it has been found that if a mixer-settler type extracting device is used, extraction is completed very easily. In case of a dilute acetic acid solution discharged from the process for manufacture of cellulose acetate, as the acetic acid concentration is lowered by extraction, dissolved fibers are precipitated. The above-mentioned mixer-settler type extracting device is especially preferably used when the above-mentioned system where transfer of the substance is inhibited by the presence of solids is treated.

The time required for bringing about the equilibrium in the mixer zone is about 2 minutes if the acetic acid concentration is as high as 30%, and at a lower acetic acid concentration, this time is further shortened and is less than 30 seconds. Accordingly, the residence time in the mixer is 1 to 2 minutes.

At the extraction step, the extraction may be performed repeatedly by using the above-mentioned mixer and settler, but when a large quantity of an acetic acid-contained aqueous solution is treated on an industrial scale, extraction is preferably carried out by the multistage counter-current extraction method. From the experimental results, it was found that the mole number of acetic acid apparently added to 1 mole of the amine and thus extracted is 1.1 at an acetic acid concentration of 2% in the aqueous phase and this mole number is gradually increased to 2.1, 3 and 3.6 as the acetic acid concentration is increased to 5%, 10% and 15%.

In this way, acetic acid is extracted in an amount larger than an amount equivalent to the amine, and furthermore the increase of the acetic acid amount gets larger as the acid concentration increases. This is an advantage when acetic acid which is present at a relatively high concentration, about 30%, must be recovered, for example acetic acid as by-produced in manufacturing cellulose acetate.

It can be said that the distribution process of acetic acid according to the invention depends on two stage model (1) the distribution equilibrium between the aqueous phase of free acetic acid and the organic phase, and (2) the reaction equilibrium in the organic phase between the free acetic acid and reaction with an amine. The oxygen-containing organic solvent to be used in the invention serves to increase a concentration of the free acetic acid, mentioned in (2), and eventually that of the combination with an amine, because a distribution coefficiency of the solvent is larger, in respect to the equilibrium mentioned as above (1), than normal hydrocarbon solvents. When a multi-stage counter-current extraction method is adopted, the extract is withdrawn from the first stage where the acetic acid concentration is highest so the number of moles of acetic acid added to the tertiary amine can be increased. The greater is the number of stages, the more increased is the extraction ratio. However, increase of the number of stages to 8 or 10 is not practically advantageous because the size of the apparatus becomes too large. In the present invention, the intended objects can satisfactorily be attained by counter-current extraction using about 5 stages, and in this case, the extraction apparatus can be used industrially conveniently.

As is seen from the foregoing description, in the present invention, extraction can be performed satisfactorily by using a mixer-settler type extracting device in the form of a multi-stage counter-current extraction apparatus including about 5 stages. Furthermore, in practising the method of the present invention, there may be adopted extracting devices arranged so that the frequency of dispersion and integration of liquid drops is enhanced and the interface is perpetually refreshed, such as RDC (rotary disc contactor) extractors, centrifugal extractors and gas-blowing stirring-type extractors.

The second step of the method of the present invention is a step of dehydration of the extract by distillation. The tertiary amine and the oxygen-containing organic solvent such as a ketone, ester or alcohol, that are used in combination as the extraction agent at the first step, should be water-insoluble compounds, but dissolution of a minute amount of water, together with acetic acid, into the extracting agent cannot be avoided even if water-insoluble compounds are used. This dissolution is especially unavoidable in the method of the present invention where in order to obtain a large apparent distribution coefficient at the extraction step, an oxygen-containing solvent is used instead of a hydrocarbon type solvent. Since the main object of the present invention is to recover water-free acetic acid, the dehydration step is very important in the present invention. An organic solvent that is used for extraction of acetic acid is ordinarily azeotropic with water, and therefore, a method in which the extract is distilled and water is removed by azeotropic boiling with the extracting agent is ordinarily adopted. However, in the case where a high-boiling-point solvent is used as in the method of the the present invention, the temperature of azeotropic boiling with water is elevated and separation of the extracting agent from acetic acid becomes difficult. In the present invention, if a part of the tertiary amine-containing extracting agent obtained from the column bottom at the third step is used as a reflux liquid fed into the dehydration column from the bottom thereof, distillate of acetic acid in the dehydration column can be prevented and separation of acetic acid from water can be performed effectively. For example, when the reflux ratio of the tertiary amine-containing extracting agent to the amount of the extract changed to the dehydration column is adjusted to at least 0.2, acetic acid is hardly observed in distilled water, and even if this reflux ratio is reduced to 0.1, the acetic acid concentration in distilled water can be controlled at 0.13%. When the reflux ratio is reduced to 0.05, the acetic acid concentration in distilled water is 0.7%. From these experimental results, it will readily be understood that recycle of a small amount of the extracting agent exerts a very high effect for separating acetic acid from water.

The third step of the method of the present invention is a step of separating intended acetic acid from the dehydrated extract by distillation and regenerating the organic extracting agent mixture as the column bottom liquid.

We made researches with a view to finding out specific conditions enabling the solvent extracting method using an amine to apply to recovery of acetic acid in the field of organic chemical industries, and as the result, we found that in order to perform the separating operation of the above-mentioned extract smoothly, selection of the kind of the amine and the distillation temperature is very important and that when an extracting agent including a primary amine or secondary amine is used, if the column bottom temperature is lowered in the distillation column, acetic acid is readily left in the column bottom liquid. From the viewpoint of the applicability of the recovery method to organic chemical industries, it is preferred that the column bottom temperature of the distillation column should be lower than 170° C. according to the pressure of steam for heating. Therefore, we made researches with a view to finding out conditions enabling acetic acid to be distilled off with no substantial residual acetic acid at a column bottom temperature lower than 170° C. As the result, we found that when a tertiary amine is used as the amine, the third step can be performed at a column bottom temperature of, for example, 120° to 150° C. while controlling the acetic acid concentration in the column bottom raffinate below 0.2%. Although the amount of residual acetic acid tends to increase with lowering of the column bottom temperature, but if the column bottom temperature is higher than about 120° C., the third step can be performed without substantial inhibition of distillation of acetic acid. The desired column bottom temperature can be realized by conducting distillation under a pressure corresponding to the composition of the extracting agent.

Most of the tertiary amines and oxygen-containing organic solvents that are used in the present invention have a relatively high boiling point. Accordingly, in order to perform distillation at a column bottom temperature of 120° to 160° C., distillation is carried out under reduced pressure. Since the boiling points of the components of the extracting agent are high, they can effectively be separated from acetic acid in the distillation column. In contrast, if a primary amine or secondary amine is used, distillation of acetic acid is difficult at a column bottom temperature of 120° to 150° C., and performance of the third step is substantially impossible.

It is preferred that a part of the regenerated extracting agent obtained from the column bottom at the third step, that is, the mixture of the oxygen-containing organic solvent and tertiary amine, be recycled to the dehydration distillation column at the second step as pointed out hereinbefore, and the remainder be used for extraction of the dilute acetic acid solution at the first step. The residual acetic acid in the recycled extracting agent has influences on the extraction efficiency. When experiment are carried out by using a mixer-settler type 5-stage extracting device, it was found that as the residual acetic acid concentration in the recycled extracting agent was increased to 0.03, 0.11, 0.2 and 0.3%, the acetic acid concentration in the residual aqueous phase was increased to 0.05, 0.07, 0.10 and 0.13%. However, it was confirmed that within this range, the extraction could be performed without any trouble and the extracting agent comprising the tertiary amine and oxygen-containing organic solvent could be recycled and used repeatedly after regeneration by distillation.

A small amount of the extracting agent is dissolved in the aqueous phase as the extraction residue (raffinate), but this extracting agent can be recovered by azeotropic boiling and distillation in the solvent recovery column.

The present invention will now be described in detail with reference to the following Examples that by no means limit the scope of the invention. Examples 1 illustrates the extraction step using an extracting agent of TOA-TMCH (50/50 volume ratio), and influences of the composition of the extracting agent and the stage number are illustrated in Example 4. When di-isobutyl carbinol or isophorone is used instead of TMCH, the extraction ratio is further improved in proportion to the improvement of the distribution coefficient. Examples 2 and 3 illustrate the step of distillation of the so obtained extracts. When a tertiary amine (having 18 to 42 carbon atoms) other than TOA is used, there are similarly obtained good results as in the case where TOA is used.

EXAMPLE 1 (EXTRACTION STEP)

An aqueous solution containing 28.1% by weight of acetic acid was charged at 30° C. at a feed rate of 201 g/hr into a counter-current type 5-stage mixer-settler type glass extracting device from the first stage tank thereof, and a mixed solvent comprising 47.0% by weight of tri-n-octylamine (TOA) and 52.5% by weight of 3,5,5-trimethylcyclohexanone (TMCH) was charged into the extracting device from the fifth stage tank in a counter-current manner at a feed rate of 210 g/hr.

The raffinate was discharged at a rate of 120 g/hr, and the acetic acid concentration in the raffinate was 0.048% by weight and it was confirmed that acetic acid was extracted substantially completely. The extract was withdrawn at a rate of 275 g/hr and the extract contained 22.01% by weight of acetic acid and 4.8% by weight of water.

COMPARATIVE EXAMPLE 1

In the same extracting device as used in Example 1, an aqueous solution containing 28.1% by weight of acetic acid was charged at 30° C. at a feed rate of 200 g/hr from the first stage tank, and ethyl acetate was charged at a feed rate of 202 g/hr in a counter-current manner from the fifth stage tank.

The raffinate was discharged at a rate of 82 g/hr and it still contained 1.01% by weight of acetic acid. The extract was withdrawn at a rate of 284 g/hr, and it contained 20.9% by weight of acetic acid and furthermore, water was contained in the extract in such a large amount as 23.3% by weight. Since a large quantity of energy is necessary for dehydration, this method is inferior to the method of Example 1 from the economical and industrial viewpoints.

EXAMPLE 2 (DEHYDRATION STEP)

The extract obtained in Example 1 (comprising 39.4% of TOA, 37.2% by weight of TMCH, 18.2% by weight of AcOH and 5.1% by weight of $H_2O$) was charged at a feed rate of 375.2 g/hr into a 40-stage perforated plate glass distillation column. A liquid comprising 53.3% by weight of TOA, 46.3% by weight of TMCH and 0.2% by weight of AcOH, which corresponded to the column bottom liquid from the acetic acid recovery column, was charged at a feed rate of 84.2 g/hr into the distillation column from the 37th stage. A liquid comprising 21.5% by weight of TMCH and 78.5% of water was distilled from the column head and acetic acid was contained in this liquid only in a trace. A liquid mixture comprising TOA, TMCH and acetic acid was withdrawn from the column bottom at a rate of 434.1 g/hr, and water was contained in this liquid only in an amount of 0.002% by weight.

EXAMPLE 3 (SEPARATION OF ACETIC ACID FROM EXTRACTING AGENT)

The residue of the dehydration column (comprising 44.4% by weight of TOA, 39.8% by weight of TMCH and 15.8% by weight of acetic acid) obtained in Example 2 was charged at a feed rate of 200 g/hr into the same distillation column as used in Example 2 from the 23rd stage. Acetic acid having a purity of 100% was distilled from the column head at a rate of 31.4 g/hr. The acetic acid concentration in the residue discharged from the bottom was 0.16% by weight.

At this step, the reflux ratio was 2 and the column head pressure was 200 mmHg.

EXAMPLE 4 (EXTRACTION STEP)

An aqueous solution containing 28% by weight of acetic acid was subjected to the extraction operation in the same manner as described in Example 1 except that the ratio of TOA in the extracting solvent, the residual acetic acid concentration in the extracting solvent and the number of extraction stages were changed as indicated in Table 1. The composition of the obtained extract and the acetic acid concentration were measured. The obtained results are shown in Table 1.

TABLE 1

| | | | Extract | | | |
|---|---|---|---|---|---|---|
| S/F | TOA/TMCH | Number of Stages | Concentration (%) of Acetic Acid | Water Content (%) | Acetic Acid Concentration (%) in Raffinate | Remarks |
| 0.75 | 50/50 | 5 | 28.0 | 6.55 | 0.17 | |
| 1.05 | 50/50 | 5 | 22.01 | 5.08 | 0.048 | |
| 1.30 | 50/50 | 5 | 18.71 | 4.59 | 0.033 | Example 1 |
| 1.68 | 50/50 | 5 | 14.24 | 3.99 | 0.015 | |
| 1.94 | 50/50 | 5 | 13.31 | 3.58 | 0.012 | |
| 1.0 | 50/50 | 5 | | | 0.072 | 0.1% of acetic acid contained in extracting agent |
| 1.22 | 50/50 | 5 | 17.99 | 4.59 | 0.06 | |
| 1.47 | 50/50 | 5 | 16.91 | 4.42 | 0.055 | |
| 0.87 | 50/50 | 3 | 24.12 | 5.70 | 0.83 | |
| 1.53 | 33/67 | 3 | 15.85 | 4.21 | 0.32 | |
| 1.24 | 25/75 | 5 | 17.32 | 4.89 | 0.075 | |
| 1.80 | 0/100 | 5 | 12.70 | 4.61 | 1.36 | |

The embodiments of the invention in which an exclusive property or privilege is claimed are defined as follows:

1. A method of recovering acetic acid by extracting an acetic acid-containing aqueous solution with an organic extracting agent and subjecting the extract to distillation, said method comprising the first step of performing extraction by using a tertiary amine having a boiling point higher than that of acetic acid and being capable of forming a non-aqueous phase as the organic extracting agent in combination with an oxygen-containing, high-boiling-point organic solvent selected from the group consisting of di-isobutyl carbinol, isophorone, methyl benzoate, tributyl phosphate, 3,3,5-trimethylcyclohexanone and 2-ethoxyethyl acetate, the second step of performing dehydration by subjecting the extract to distillation, and the third step of subjecting the dehydrated mixture to distillation in a reduced pressure distillation column at a column bottom temperature of 120° to 170° C. to distill acetic acid and separate it from the organic extracting agent.

2. A recovery method according to claim 1, wherein the organic extracting agent separated from acetic acid at the third step is used as a reflux liquid to be fed to the distillation column of the second step.

3. A recovery method according to claim 1, wherein the acetic acid concentration in the starting aqueous solution is 7 to 40% by weight.

4. A recovery method according to claim 1, wherein the extraction of the first step is carried out by using a mixer-settler type counter-current multi-stage extracting device.

5. A recovery method according to claim 1, wherein the tertiary amine has 12 to 40 carbon atoms and in the partial structure $>$N-CH$_2$CR$^1$R$^2$- of said tertiary amine, R$^1$ is a hydrogen atom and R$^2$ is a hydrogen atom or a methyl group.

6. A recovery method according to claim 5, wherein the tertiary amine is tri-n-octylamine.

7. A recovery method according to claim 1, wherein the oxygen-containing organic solvent is 3,3,5-trimethylcyclohexanone.

8. A recovery method according to claim 1, wherein the oxygen-containing organic solvent is a member selected from the group consisting of isophorone, 2-ethoxethyl acetate, methyl benzoate and tributyl phosphate.

9. A recovery method according to claim 1, wherein the oxygen-containing organic solvent is di-isobutyl carbinol.

10. A recovery method according to claim 1, wherein the proportion of the tertiary amine in the extraction solvent is 10 to 80% by volume.

11. A recovery method according to claim 10, wherein the proportion of the tertiary amine in the extraction solvent is 50% by volume.

12. A recovery method according to claim 1, wherein the extraction of the first step is carried out at a temperature not higher than 50° C.

13. A recovery method according to claim 1, wherein the third step is conducted at a column bottom temperature of 120° to 150° C.

* * * * *